United States Patent [19]

Munn

[11] Patent Number: 5,415,859
[45] Date of Patent: May 16, 1995

[54] PRODUCTION AND USE OF ANTHELMINTIC AGENTS AND PROTECTIVE ANTIGENS

[76] Inventor: Edward A. Munn, 72 Station Road, Fulbourn, Cambridge CB1 5ES, Cambridgeshire, England

[21] Appl. No.: 928,187

[22] Filed: Aug. 14, 1992

Related U.S. Application Data

[63] Continuation of Ser. No. 481,698, Feb. 20, 1990, abandoned, which is a continuation of Ser. No. 295,185, Dec. 29, 1988, abandoned.

[30] Foreign Application Priority Data

Aug. 7, 1986 [GB] United Kingdom ............. 8619293

[51] Int. Cl.⁶ .................. C07K 15/08; C07K 3/22; C07K 3/28; A61K 39/00
[52] U.S. Cl. ................ 424/265.1; 530/350; 530/412; 530/416; 530/417; 530/418; 530/422; 530/427; 530/806
[58] Field of Search .......... 424/88, 265.1; 530/412, 530/416, 417, 427, 418, 422, 350, 806

[56] References Cited

U.S. PATENT DOCUMENTS 3,395,218 7/1968 Silverman ............... 424/88

OTHER PUBLICATIONS

Emery et al., 1991, Parasitology, Today, 7(12):347–349.
Salem et al., 1984, J. Biol. Chem., 259(19):12246–12251.
Martin et al., 1986, J. Biol. Chem. 261(19):8754–8760.
Clarke et al., 1984, Abstract of Can. J. Comp. Med., 48(2):166–170, Biological Abstract, vol. 78, No. 59955.
E. A. Munn et al., Parasitology (1987), 94:385–397, Vaccination of young lambs by means of a protein fraction extracted from adult *Haemonchus contortus*.

Primary Examiner—Keith C. Furman
Attorney, Agent, or Firm—Nikaido, Marmelstein, Murray & Oram

[57] ABSTRACT

The protein doublet H110D, the individual components thereof, and the production and use thereof in a vaccine against a nematode infection. This protein doublet is a plasma membrane-associated protein material of the intestinal microvilli of *Haemonchus contortus*. H110D has a molecular weight of about 110 kd and reacts with antibodies raised in animals injected with a contortin-enriched fraction. Injection of preparations of the protein doublet H110D or its components induces the production of specific protective antibodies.

15 Claims, 1 Drawing Sheet

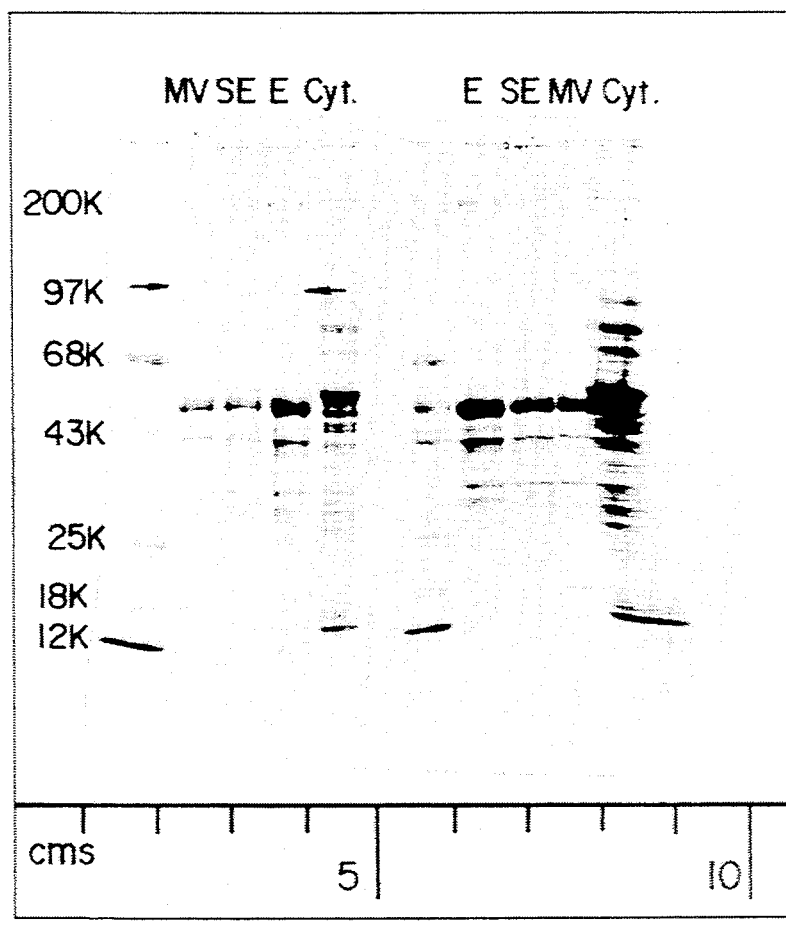

PRODUCTION AND USE OF ANTHELMINTIC AGENTS AND PROTECTIVE ANTIGENS

This application is a continuation of application Ser. No. 481,698, filed Feb. 20, 1990, now abandoned, which in turn is a continuation of application Ser. No. 295,185, filed Dec. 29, 1988, now abandoned.

BACKGROUND OF THE INVENTION

1. Field of the Invention

This invention relates to production of materials for study as potential anthelmintic agents and as protective antigens.

2. Prior Art

Nematodes are parasites which are found in farm animals and in man and are the cause of disease therein.

Haemonchosis is a disease of ruminants due to the presence, in the gastro-intestinal tract, of the blood-feeding nematode Haemonchus. World-wide it is of very considerable economic importance having effects which range from reduction in weight gain, loss of production and agalactia through to death of domesticated animals. Ostertagiasis is caused by a related nematode Ostertagia and has similar effects. Both diseases are characterised by wasting due in part to anorexia associated with severe infections. In sheep and cattle, Ostertagia is the most important in winter rainfall areas, while Haemonchus is more important in summer rainfall zones. In Australia, for example, it is estimated that approximately one third of the 300 million sheep in the country are likely to be infected with Haemonchus.

The adult female of the nematode Haemonchus is up to 3 cm long and about 1 mm wide and has a diagonal red and white striped appearance. For this reason it is sometimes known as the barber's pole worm. The red colour is due to the presence of the host's blood in the intestine of the parasite. The parasitic stage of the worm lives attached to the wall of the stomach of the host animal, e.g. sheep, goat or cow, which it damages causing loss of blood in addition to that which it ingests. The animal becomes infected by ingesting infective larvae as it grazes on infested pastures. In the rumen the larva moults and passes into the abomasum where it develops, attaches itself to the stomach wall and commences ingesting blood. Over the following 7 days or so it continues to grow and then moults to give the young adult stage. About 18 to 21 days after infection it has become sexually mature and mates. The eggs pass out with the host faeces and hatch in due course into free-living larvae which develop into infective larvae.

Ostertagia differs from Haemonchus in that it feeds on the host animal's plasma, not on its blood. It has a smaller intestine than Haemonchus.

Although control of nematodes, such as Haemonchus and Ostertagia, can be achieved in sheep and cattle by administration of anthelmintic drugs, this approach is far from satisfactory as repeated dosing is necessary in order to achieve any degree of control over an infestation in a flock of sheep or herd of cattle.

Numerous attempts have been made to develop vaccines to Haemonchus and to Ostertagia including use of attenuated live worms and extracts of the worms. However, so far a commercially successful vaccine has not yet been produced. Although injection of extracts of various kinds produced from Haemonchus or Ostertagia has in some cases led to generation of antibodies directed against the parasite, such antibodies appear to be similar to those formed by natural infection and do not seem to enhance natural resistance to the parasite.

I have previously reported in "Tissue & Cell", 1977, 9 (1) at pages 23 to 34, the existence of a helical, polymeric extracellular protein which is associated with the luminal surface of Haemonchus contortus intestinal cells. In the fourth stage larvae and adult nematodes (the parasitic stages) the microvilli on the intestinal cells of Haemonchus contortus have associated therewith filaments in the form of helices about 400Å in diameter and of variable pitch. These filaments proved to be primarily protein which I designated as contortin. On page 24 of the paper cited above, "Tissue & Cell" 1977 9(1), pages 23–34, a process for preparing contortin is described. In this process, approximately 2 g net weight adult Haemonchus contortus were homogenized in 60 ml 10 nM phosphate buffered saline (pH 7.3). The homogenate was centrifuged for 5 minutes at 3000 rpm in a 6450 rotor of an MSE Minor centrifuge at 4° C. The supernatant was decanted and the pellets homogenized again and the homogenate re-centrifuged. The pooled supernatants were centrifuged at 10000 g for 10 minutes in a SS-34 rotor of a Sorvall RC-2 refrigerated centrifuge. The pellets were washed once on the centrifuge and the pooled supernatants centrifuged for 90 minutes at 50000 rpm in a Type 50 rotor of a Bechman Spinco Model L centrifuge. The sedimented material contained the bulk of the contortin in its extracellular form as judged by electron microscopy of negatively stained samples.

Further investigation showed that the helical filament of contortin appears to be formed by lateral polymerization of a monomeric form which has a Y-shaped structure with arms about 45 Å long and 25 Å wide seen in negatively stained preparations. A further description of contortin appeared in "Proceedings of the Sixth European Congress on Electron Microscopy", Vol II, pages 515 and 516. Ostertagia circumcincta also has contortin-like material associated with the microvilli in its intestine.

A brief report that antibodies against contortin have been raised in rabbits with a view to testing whether contortin is antigenic and would act as a vaccine in sheep appeared in the "Report for 1974–75" of the Agricultural Research Council Institute of Animal Physiology, Babraham, in June 1976. In the corresponding "Report for 1976–77" published in 1978, there were summarised on page 94 the results of furthest work by me in which I showed that intramuscular injection of contortin-enriched fractions into young lambs gave a substantial measure of protection against haemonchosis when they were subsequently challenged with larvae of Haemonchus contortus. This work on the use of a contortin-enriched preparation for protection against haemonchosis has been published in "Parasitology", 94, at pages 385 to 397.

Although a contortin-enriched fraction can be used to protect lambs against infection by Haemonchus contortus, such a fraction is not commercially useful as it has generally required injection of a large quantity of such a fraction in order to produce in the animal a suitable immune response. Moreover it is difficult to obtain either the polymeric or monomeric form of contortin in purer form and in sufficient quantity to facilitate further study of their antigenic characteristics.

There is also present in the supernatant liquor from which contortin is obtained by the procedure described in the afore-mentioned article in "Tissue & Cell" and "Parasitology", a further material which appears to be primarily protein, which has a molecular weight of approximately 61,000, and which reacts with antibodies to contortin. This protein I have named pre-contortin.

SUMMARY OF THE INVENTION

There is a need to provide proteins which can be used as protective antigens to form the basis of vaccines against nematode infections in sheep, cattle and man.

The present invention accordingly seeks to provide novel protein extracts from nematodes which have potential as protective antigens against such nematode infections.

DESCRIPTION OF THE DRAWING FIGURE

The accompanying FIGURE is a photograph of the electrophoretogram revealed by staining for protein following electrophoresis of various extracts on polyacrylamide gel. The unlabeled pattern at the left of the FIGURE is given by a mixture of standard proteins of known molecular weight. The other designations are as follows:
MV=microvilli
SE=scraped endotube
E=endotube (with attached microvilli)
Cyt=basal cytoplasm
The H110D doublet is indicated by the arrows.

DETAILED DESCRIPTION OF THE INVENTION

The present invention is based upon the surprising discovery that a membrane associated protein material present in the microvilli of *Haemonchus contortus* exhibits a strong antibody reaction with antibodies raised in sheep using a contortin-enriched fraction. This material appears as a double band upon SDS (sodium dodecyl sulphate)-polyacrylamide gel electrophoresis of a protein fraction obtained by extraction of the microvilli of *Haemonchus contortus* with a solution of a non-ionic detergent. By comparison with the mobility of proteins of known molecular weight the apparent molecular weight of this double band is approximately 110 Kilodaltons.

I have given this protein doublet the name H110D.

According to one aspect of the present invention I provide the protein doublet H110D. I also provide the individual components thereof. Such components include both the protein present in the protein doublet that has the higher molecular weight of the two bands apparent upon subjection to SDS-polyacrylamide gel electrophoresis and also the protein of the other band with the lower apparent molecular weight.

The invention further provides a method of preparing a membrane associated protein comprising homogenizing nematodes in a liquid carrier, centrifuging resulting homogenate to separate suspended cell debris, extracting the separated cell debris with a solution of a non-ionic detergent to solubilise membrane protein material, separating the extracted cell debris from a first supernatant liquor, subjecting resulting first supernatant liquor to ultracentrifugation, separating sedimented material, recovering a second supernatant liquor containing membrane associated proteins, and separating from the second supernatant liquor, a protein or proteins having an apparent molecular weight, upon subjection to polyacrylamide gel electrophoresis in the presence of sodium dodecyl sulphate, of approximately 110 kd. The protein or proteins prepared in this way exhibit a strong positive reaction in vitro with antibodies raised in sheep by injection of a contortin-enriched fraction. When the nematodes used are *Haemonchus contortus*, the protein doublet H110D can be isolated from the supernatant liquor from the ultracentrifugation step by conventional methods such as gel electrophoresis, iso-electric focussing, gel exclusion chromatography, ion exchange chromatography, and methods based on hydrophobicity. It can be identified as a double band which corresponds to a molecular weight of approximately 110 kd by SDS-polyacrylamide gel electrophoresis.

The protein doublet H110D is further characterised by the existence of a strong positive reaction in vitro with antibodies raised in sheep by injection of a contortin-enriched fraction obtained from a homogenate of *Haemonchus contortus*. The strength of the antibody response indicates that the protein doublet H110D, or one of its components, may be a beneficial protective antigen which could form a basis for a vaccine against Haemonchus and possibly also against other nematodes such as Ostertagia. I have demonstrated the value of preparations of H110D as protective antigens by injection of both partially purified and highly purified preparations into lambs which responded by production of specific antibodies and were then very substantially protected against haemonchosis when they were subsequently challenged with larvae of *Haemonchus contortus*.

The microvilli on the intestinal wall of *Haemonchus contortus* are relatively long. Electron microscopy thereof reveals that each microvillus has an axial core (which extends below the base of the microvillus to join a fibrous layer called the endotube), a plasma membrane, cross linker proteins which join the axial core to the membrane, and helically coiled contortin molecules adjacent to the external surface of the membrane. The endotube with the attached microvilli can be separated from the remaining, basal, cytoplasm of the intestine. The microvilli can be separated from the endotube of *Haemonchus contortus* by appropriate manipulative techniques. One method involves contacting the endotube and its attached microvilli with a solution of dithiothreitol and carefully scraping the microvilli off the endotube with a probe whilst observing the endotube surface under a microscope. As will be apparent to the skilled reader this technique is tedious and it is somewhat time consuming to obtain more than a small amount of material in this way. Analysis of a preparation of such microvilli indicated the presence of three major proteins, namely contortin, actin and a previously unidentified protein material which shows up as a doublet band with an apparent molecular weight of approximately 110 kd upon SDS-polyacrylamide gel electrophoresis. By analogy with microvilli from mammalian and avian species this unidentified protein material would be expected to correspond to the cross linker protein or proteins. However, further investigation shows surprisingly that this is not the case. Instead the 110 kd doublet band, which I have designated H110D, proves to be a membrane associated protein material. This can be demonstrated by extraction of a sample with a non-ionic detergent solution, specifically either a 1% w/v TRITON X-100, THESIT, CHAPS (i.e. 3-[(3-cholamidopropyl)dimethylammonio]propanesulphonate), or n-octyl glucoside solution containing protease inhibitors (the words "TRITON" and "THESIT" are trade marks). This extraction step can be carried out with or without pre-extraction with high salt and TWEEN 20 solutions (the word "TWEEN" is a trade mark). It dissolves the membrane protein material but, as can be seen by electron microscopy, leaves the cross linker proteins and axial core (presumably actin) intact.

Close examination of microvilli of *Haemonchus contortus* by electron microscopy using a negative staining technique reveals particles on the membrane surface which are immediately adjacent to the helically coiled contortin molecules. It seems likely that these particles correspond to the protein material of the doublet H110D.

It is further contemplated that, in an alternative method of preparing the protein doublet H110D, *Haemonchus contortus* is replaced by another nematode, for example by another species of Haemonchus or by one or more species of Ostertagia or some other nematode, which is then subjected to homogenization, extraction, centrifugation and the other steps outlined above for preparing the protein doublet H110D from *Haemonchus contortus*. Also, the detergent may be replaced by another detergent, preferably another non-ionic detergent.

The invention also provides a vaccine comprising the protein doublet H110D, either alone or in conjunction with contortin. It also provides vaccines comprising the individual protein components of the protein doublet H110D, either by themselves or in conjunction with contortin. Hence there is provided a vaccine based on the protein of the doublet H110D that has the higher molecular weight of the two bands apparent upon subjection to polyacrylamide gel electrophoresis, either alone or in conjunction with contortin. Similarly there is provided a vaccine based upon the protein of the doublet H110D that has the lower molecular weight of the two bands apparent upon subjection to polyacrylamide gel electrophoresis, either alone or in conjunction with contortin. It also includes vaccines based upon mixtures of these two proteins in any proportion, either alone or in conjunction with contortin. Such vaccines are useful in the treatment of haemonchosis, ostertagiasis and other diseases caused by nematodes in farm animals and in man.

The invention is further illustrated in the following Example.

EXAMPLE

Approximately 2 g live weight adult *Haemonchus contortus* were homogenized in 60 ml 10 mM phosphate buffered saline (pH 7.3). The resulting homogenate was centrifuged for 10 minutes at 10000 rpm at 4° C. The supernatant liquid was decanted and the pellets homogenized again and the homogenate re-centrifuged. The pellets were then extracted with 20 ml of a 1% TWEEN 20 solution and re-centrifuged. The supernatant liquor was discarded. The pellets were then extracted with 20 ml of a 1% w/v THESIT solution. (The word "THESIT" is a trade mark: THESIT is a non-ionic detergent). The resultant extract was centrifuged at 10,000 g for 10 minutes in a refrigerated centrifuge. The supernatant liquor was poured off the resulting sediment and then centrifuged for approximately $11 \times 10^6$ g.min. The sedimented material was discarded. Part of the supernatant liquor was subjected to electrophoresis on polyacrylamide gel in the presence of sodium dodecyl sulphate. The protein doublet, H110D, was identified as a double band corresponding to a molecular weight of about 110 kd by a conventional staining technique and was eluted. The other part of the supernatant liquor was fractionated by gel exclusion and ion exchange chromatography and the fractions containing H110D were pooled and concentrated.

Small amounts of these materials injected into lambs induced the formation of specific antibodies and the subsequent protection of the animals against haemonchosis. This result demonstrates that the protein doublet H110D is a protective antigen.

I claim:

1. A purified and isolated protein doublet H110D obtainable by isolation from the microvillus of Haemonchus, which protein doublet moves as two bands upon subjection to polyacrylamide gel electrophoresis in the presence of sodium dodecyl sulphate and which has an apparent molecular weight of about 110 kd.

2. The protein doublet of claim 1, wherein said nematode is *Haemonchus contortus*.

3. A vaccine for immunizing ruminant animals against Haemonchus infection comprising an amount effective to immunize said animal of a purified and isolated protein doublet H110D obtainable by isolation from the intestinal microvilli of Haemonchus, which protein doublet moves as two bands upon subjection to polyacrylamide gel electrophoresis in the presence of sodium dodecyl sulphate and which has an apparent molecular weight of about 110 kd, in combination with a suitable pharmaceutical carrier.

4. A vaccine for immunizing ruminant animals against *Haemonchus contortus* infection comprising an amount effective to immunize said animal of a purified and isolated protein doublet H110D obtainable by isolation from the intestinal microvilli of *Haemonchus contortus*, which protein doublet moves as two bands upon subjection to polyacrylamide gel electrophoresis in the presence of sodium dodecyl sulphate and which has an apparent molecular weight of about 110 kd, in combination with a suitable pharmaceutical carrier.

5. A vaccine for immunizing ruminant animals against Haemonchus or infection comprising a purified and isolated protein doublet H110D obtainable by isolation from the microvillus of Haemonchus, which protein doublet moves as two bands upon subjection to polyacrylamide gel electrophoresis in the presence of sodium dodecyl sulphate and which has an apparent molecular weight of about 110 kd and contortin.

6. A vaccine for immunizing ruminant animals against *Haemonchus contortus* infection comprising a purified and isolated protein doublet H110D obtainable by isolation from the microvillus of *Haemonchus contortus*, which protein doublet moves as two bands upon subjection to polyacrylamide gel electrophoresis in the presence of sodium dodecyl sulphate and which has an apparent molecular weight of about 110 kd and contortin.

7. A method of immunizing ruminant animals against Haemonchus infection comprising administering to a ruminant animal in need of immunization, a purified and isolated protein doublet H110D obtainable by isolation from the intestinal microvilli of Haemonchus, which protein doublet moves as two bands upon subjection to polyacrylamide gel electrophoresis in the presence of sodium dodecyl sulphate and which has an apparent molecular weight of about 110 kd, in an amount effective to immunize said animal against said Haemonchus infection.

8. A method of immunizing ruminant animals against *Haemonchus contortus* infection comprising administering to a ruminant animal in need of immunization, a purified and isolated protein doublet H110D obtainable by isolation from the intestinal microvilli of *Haemonchus contortus*, which protein doublet moves as two bands upon subjection to polyacrylamide gel electrophoresis in the presence of sodium dodecyl sulphate and which has an apparent molecular weight of about 110 kd, in an amount effective to immunize said animal against said *Haemonchus contortus* infection.

9. A method of immunizing ruminant animals against Haemonchus infection comprising administering to a ruminant animal in need of immunization a purified and isolated protein doublet H110D obtainable by isolation from the intestinal microvilli of Haemonchus, which protein doublet moves as two bands upon subjection to polyacrylamide gel electrophoresis in the presence of sodium dodecyl sulphate and which has an apparent molecular weight of about 110 kd and contortin, in amounts effective to immunize said animal against said Haemonchus infection.

10. A method of immunizing ruminant animals against *Haemonchus contortus* infection comprising administering to a ruminant animal in need of immunization a purified and isolated protein doublet H110D obtainable by isolation from the intestinal microvilli of *Haemonchus contortus*, which protein doublet moves as two bands upon subjection to polyacrylamide gel electrophoresis in the presence of sodium dodecyl sulphate and which has an apparent molecular weight of about 110 kd and contortin, in amounts effective to immunize said animal against said *Haemonchus contortus* infection.

11. A method of preparing a membrane associated protein comprising homogenizing Haemonchus nematodes in a liquid carrier, centrifuging resulting homogenate to separate suspended cell debris, extracting the separated cell debris with a solution of a non-ionic detergent to solubilise membrane protein material, separating the extracted cell debris from a first supernatant liquor, subjecting resulting first supernatant liquor to ultracentrifugation, separating sedimented material, recovering a second supernatant liquor containing membrane associated proteins, and separating from the second supernatant liquor a protein or proteins having an apparent molecular weight, upon subjection to polyacrylamide gel electrophoresis in the presence of sodium dodecyl sulphate, of approximately 110 kd.

12. A method according to claim 11, in which the nematodes are *Haemonchus contortus*.

13. A method according to claim 11 or 12, in which the step of separating the said protein or proteins from the second supernatant liquor is accomplished by a method which is at least one selected from the group consisting of gel electrophoresis, gel exclusion chromatography, ion exchange chromatography, iso-electric focussing, and a method based on hydrophobicity.

14. A purified and isolated protein produced by a method according to claim 13 which has an apparent molecular weight, upon subjection to polyacrylamide gel electrophoresis in the presence of sodium dodecyl sulphate, of approximately 110 kd.

15. A purified and isolated protein doublet H110D prepared by a method according to claim 13 which protein doublet moves as two bands upon subjection to polyacrylamide gel electrophoresis in the presence of sodium dodecyl sulphate and which has an apparent molecular weight of about 110 kd.

* * * * *

UNITED STATES PATENT AND TRADEMARK OFFICE
CERTIFICATE OF CORRECTION

PATENT NO. : 5,415,859
DATED : May 16, 1995
INVENTOR(S) : MUNN

It is certified that error appears in the above-indentified patent and that said Letters Patent is hereby corrected as shown below:

On the title page, item [30] should read as follows:
[30] PCT  PCT/GB87/00561 Aug. 7, 1987

Signed and Sealed this

Eleventh Day of June, 1996

Attest:

BRUCE LEHMAN

*Attesting Officer*       *Commissioner of Patents and Trademarks*